United States Patent
Faghihnejad et al.

(10) Patent No.: US 10,400,180 B2
(45) Date of Patent: Sep. 3, 2019

(54) METHOD FOR SIMULATING HIGH PRESSURE PARAFFINIC FROTH TREATMENTS

(71) Applicant: Ecolab USA Inc., St. Paul, MN (US)

(72) Inventors: Ali Faghihnejad, Edmonton (CA); Meng Luo, Edmonton (CA); Song Gao, Sherwood Park (CA); Anoop Chengara, Buffalo Grove, IL (US)

(73) Assignee: Ecolab USA Inc., St. Paul, MN (US)

( * ) Notice: Subject to any disclaimer, the term of this patent is extended or adjusted under 35 U.S.C. 154(b) by 249 days.

(21) Appl. No.: 15/282,285

(22) Filed: Sep. 30, 2016

(65) Prior Publication Data

US 2017/0096607 A1 Apr. 6, 2017

Related U.S. Application Data

(60) Provisional application No. 62/235,982, filed on Oct. 1, 2015.

(51) Int. Cl.
| | | |
|---|---|---|
| *C10G 29/20* | (2006.01) | |
| *C10G 29/28* | (2006.01) | |
| *G01N 11/00* | (2006.01) | |

(52) U.S. Cl.
CPC .............. *C10G 29/28* (2013.01); *C10G 29/20* (2013.01); *G01N 11/00* (2013.01); *C10G 2300/206* (2013.01); *G01N 2011/0046* (2013.01)

(58) Field of Classification Search
CPC ........ C10G 1/045; C10G 29/20; C10G 29/28; C10G 2300/206; C10G 2300/302; C10C 3/026; G01N 11/00
See application file for complete search history.

(56) References Cited

U.S. PATENT DOCUMENTS

| | | | |
|---|---|---|---|
| 5,021,498 A | 6/1991 | Stephenson et al. | |
| 5,236,577 A | 8/1993 | Tipman et al. | |
| 6,187,172 B1 | 2/2001 | Plummer | |
| 6,783,582 B2 | 8/2004 | Goldman | |
| 8,252,170 B2 | 8/2012 | Sharma et al. | |
| 8,709,237 B2 | 4/2014 | Stevens et al. | |
| 9,315,718 B2* | 4/2016 | Soane ................... | C09K 8/584 |

FOREIGN PATENT DOCUMENTS

| | | | |
|---|---|---|---|
| CA | 2232929 | 3/1998 | |
| CA | 2217300 | 9/1999 | |
| CA | 2502329 A1 * | 9/2006 | ............ C10G 1/045 |
| CA | 2502329 A1 | 9/2006 | |
| CA | 2587166 A1 | 9/2007 | |

OTHER PUBLICATIONS

International Search Report dated Jan. 11, 2017 relating to PCT Application No. PCT/US2016/054932, 4 pages.
Written Opinion dated Jan. 11, 2017 relating to PCT Application No. PCT/US2016/054932, 6 pages.

* cited by examiner

*Primary Examiner* — Randy Boyer
(74) *Attorney, Agent, or Firm* — Stinson LLP

(57) ABSTRACT

The present invention generally relates to methods for decreasing viscosity, yield stress, or viscosity and yield stress of an asphaltene precipitate-containing aqueous mixture. More specifically, the method comprises applying an effective amount of a water-soluble polymer to an asphaltene precipitate-containing aqueous mixture. The water-soluble polymers comprise polyanion, polycation, and polar water-soluble polymer components. The present invention also relates to water-soluble asphaltene dispersants.

19 Claims, 2 Drawing Sheets

1 - Nitrogen supply line
2 - Inlet line
3 - Reaction mixture
4 - Outlet line
10, 15, 20, 25, 30, 35 - Valve
40 - High-pressure sampling cylinder
45 - Pressure gauge
50 - Temperature gauge 55 - Controller
60 - Mixer
65 - Reactor
70 - Hot water jacket
75 - Water bath
80 - Ice bath
85 - Cooling coil
90 - Overflow sample collector

METHOD FOR SIMULATING HIGH PRESSURE PARAFFINIC FROTH TREATMENTS

CROSS-REFERENCE TO RELATED APPLICATION

This application claims priority to U.S. Provisional Patent Application Ser. No. 62/235,982 filed on Oct. 1, 2015, the disclosure of which is incorporated herein by reference in its entirety.

FIELD OF THE INVENTION

The present invention generally relates to methods for decreasing viscosity or yield stress of an asphaltene precipitate-containing aqueous mixture. More specifically, the method comprises applying an effective amount of a water-soluble polymer to an asphaltene precipitate-containing aqueous mixture. The water-soluble polymers comprise polyanion, polycation, and polar water-soluble polymer components. The present invention also relates to water-soluble asphaltene dispersants.

BACKGROUND OF THE INVENTION

Paraffinic froth treatments are used within the petroleum industry to eliminate aqueous and solid contaminants (i.e., asphaltenes) from the froth to form a clean bitumen product. Paraffinic solvents can be added to reduce viscosity and density of the oil phase, to produce a diluted bitumen product. The diluted bitumen can be transported more effectively and economically through pipelines.

Even though, paraffinic froth treatments are able to clean the bitumen product and reject asphaltene deposits, large asphaltene, and solid aggregates can still form in the bottom of the froth settling units (FSU), which can lead to plugging of equipment and pipelines. Large asphaltene and solid aggregates that are carried over to the tailings solvent recovery system (TSRU) can hinder solvent recovery and cause foaming within the TSRU.

Asphaltenes are defined as the crude oil fraction that is soluble in aromatic solvents and insoluble in low-boiling straight chain alkanes. Asphaltene molecules have complex structures and are typically polar molecules with relatively high molecular weights (approximately 700 to 1,000 g/mole). Asphaltenes can contain carbon, hydrogen, nitrogen, oxygen, and sulfur, as well as trace amounts of vanadium and nickel.

Asphaltenes are typically stable under virgin reservoir conditions, but can be destabilized and precipitate from crude oil during production due to changes in temperature, pressure, chemical composition, and shear rate. Asphaltene deposits can occur throughout the production system, from inside the reservoir formation to pumps, tubing, wellheads, safety valves, flow lines, and surface facilities used in the extraction process. Asphaltene deposits can cause production rate decline and other operational problems, such as increased fluid viscosity and density, and stabilization of oil-water emulsions. The nature of asphaltene deposits, which can appear hard and coal-like or sticky and tar-like, is determined by the composition of the crude oil and the conditions under which precipitation occurred. Asphaltene deposits can block reservoir pores in near-well formations, production tubing, and downstream pipelines.

Therefore, a need exits to develop methods and chemistries for increasing the fluidity of the underflow, decreasing asphaltene formation, and enhancing solvent recovery.

SUMMARY OF THE INVENTION

One aspect of the invention is a method for decreasing viscosity, decreasing yield stress, or decreasing viscosity and yield stress of an asphaltene precipitate-containing aqueous mixture. The method comprises mixing an asphaltene-containing hydrocarbon with paraffinic solvent to form the asphaltene precipitate-containing aqueous mixture and contacting an effective amount of a water-soluble polymer with the asphaltene precipitate-containing aqueous mixture whereby the viscosity, the yield stress, or the viscosity and the yield stress of the asphaltene precipitate-containing aqueous mixture is reduced as compared to an otherwise identical asphaltene precipitate-containing aqueous mixture without the water-soluble polymer when measured at a temperature from about 20° C. to about 150° C.

Another aspect of the invention is a method for determining viscosity or yield stress of an asphaltene precipitate-containing aqueous mixture. The method comprises charging a bitumen froth into a high pressure reactor fitted with a mixer and a temperature controller; charging a paraffinic solvent into a sampling cylinder in fluid contact with the high pressure reactor; heating the high pressure reactor to a temperature of from about 30° C. to about 95° C.; pressurizing the high pressure reactor by adding gas from a gas source in fluid contact with the high pressure reactor; contacting the paraffinic solvent with the bitumen froth to form a reaction mixture; mixing the reaction mixture; stopping the mixing and allowing the solids, water, and asphaltene precipitates to separate from the bitumen forming a bitumen layer and an aqueous layer; removing at least a portion of the bitumen layer from the high pressure reactor; contacting an effective amount of a water-soluble polymer for reducing viscosity, yield stress, or viscosity and yield stress with the aqueous layer; contacting additional paraffinic solvent with the remaining bitumen layer and aqueous layer to form a second reaction mixture; reheating the high pressure reactor to a temperature of from about 30° C. to about 95° C.; repressurizing the high pressure reactor by adding gas from a gas source in fluid contact with the high pressure reactor; mixing the second reaction mixture; stopping the mixing and allowing the water and asphaltene precipitates to separate from the bitumen forming a second bitumen layer and a second aqueous layer; removing at least a portion of the second bitumen layer from the high pressure reactor; and measuring viscosity or yield stress of the second aqueous layer.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
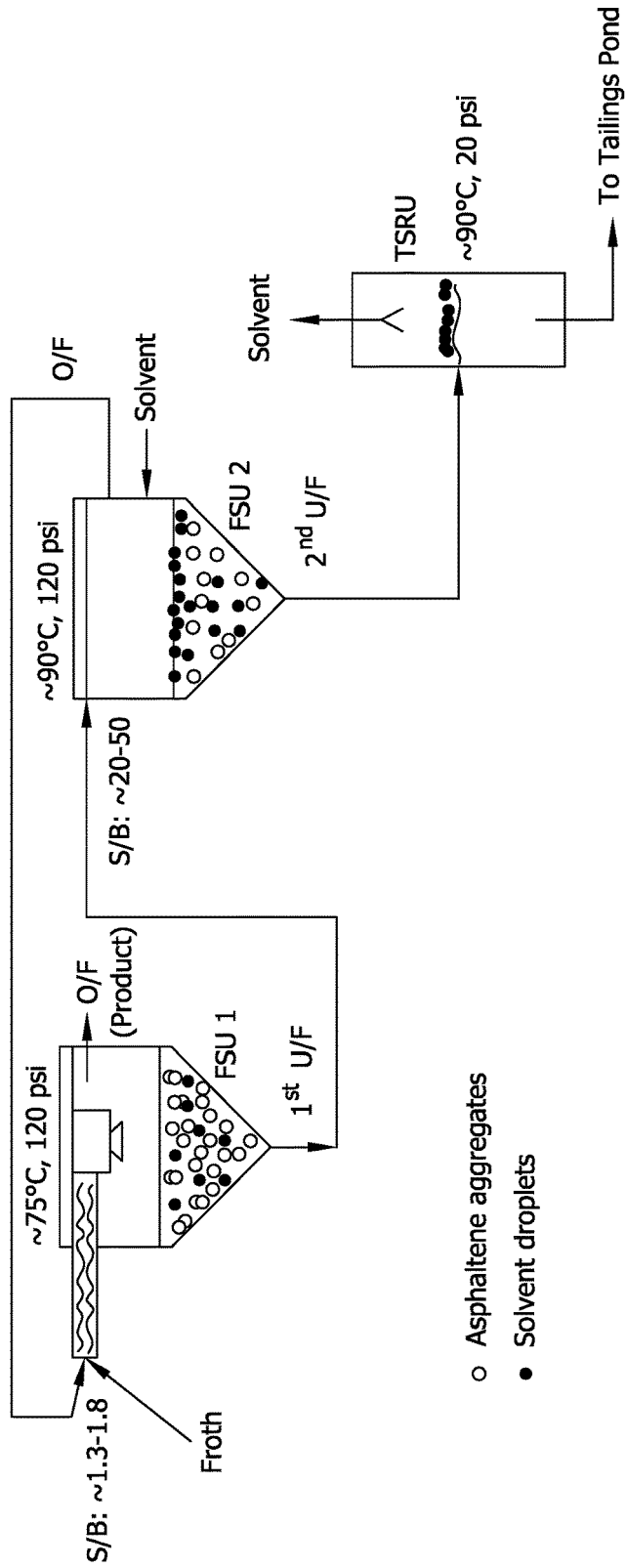
FIG. 1 is a diagram of the high temperature paraffinic froth treatment process.

The present invention is directed towards methods for decreasing viscosity, yield stress, or viscosity and yield stress of an asphaltene precipitate-containing aqueous mixture. An effective amount of a water-soluble polymer that is not ethoxylated is contacted with the asphaltene precipitate-containing aqueous mixture whereby the viscosity, yield stress, or viscosity and yield stress of the aqueous mixture is reduced as compared to an otherwise identical asphaltene precipitate-containing aqueous mixture without the water-soluble polymer when measured at a temperature from about 20° C. to about 150° C.

The asphaltene precipitate-containing aqueous mixture can further comprise solids, and hydrocarbons.

The asphaltene precipitate-containing aqueous mixture can be from the underflow of a froth settling unit in a paraffinic solvent froth treatment.

The underflow can be from a second froth settling unit in the paraffinic solvent froth treatment.

The underflow from the second froth settling unit can be transferred to the tailings solvent recovery unit.

The asphaltene precipitate-containing aqueous mixture in the tailings solvent recovery unit can have a reduced viscosity as compared to the otherwise identical asphaltene precipitate-containing aqueous mixture without the water-soluble polymer when measured at a temperature from about 20° C. to about 150° C., from about 20° C. to about 120° C., from about 20° C. to about 100° C., from about 20° C. to about 80° C., from about 40° C. to about 150° C., from about 40° C. to about 120° C., from about 40° C. to about 100° C., from about 40° C. to about 80° C., from about 50° C. to about 150° C., from about 50° C. to about 120° C., from about 50° C. to about 100° C., from about 50° C. to about 80° C., from about 50° C. to about 70° C., from about 55° C. to about 65° C., or about 60° C.

The asphaltene precipitate-containing aqueous mixture in the tailings solvent recovery unit can have a reduced viscosity as compared to the otherwise identical asphaltene precipitate-containing aqueous mixture without the water-soluble polymer when measured at a pressure from about 15 psi to about 150 psi, from about 15 psi to about 130 psi, from about 15 psi to about 110 psi, from about 15 psi to about 90 psi, from about 15 psi to about 80 psi, from about 30 psi to about 150 psi, from about 30 psi to about 130 psi, from about 30 psi to about 110 psi, from about 30 psi to about 90 psi, from about 30 psi to about 85 psi, from about 50 psi to about 150 psi, from about 50 psi to about 130 psi, from about 50 psi to about 110 psi, from about 50 psi to about 90 psi, from about 50 psi to about 85 psi, from about 70 psi to about 150 psi, from about 70 psi to about 130 psi, from about 70 psi to about 110 psi, from about 70 psi to about 90 psi, from about 70 psi to about 85 psi, from about 75 psi to about 85 psi, or about 80 psi.

When the viscosity is measured at a temperature from about 55° C. to about 65° C., a pressure from about 75 psi to about 85 psi, and a mixing rate from about 550 rpm to about 650 rpm, the viscosity is reduced by about 75%, about 70%, about 65%, about 60%, about 55%, about 50%, about 45%, about 40%, about 35%, about 30%, about 25%, or about 20%.

The asphaltene precipitate-containing aqueous mixture in the tailing solvent recovery unit has a reduced yield stress as compared to an otherwise identical asphaltene precipitate-containing aqueous mixture without the water-soluble polymer when measured at a temperature from about 20° C. to about 150° C., from about 20° C. to about 120° C., from about 20° C. to about 100° C., from about 20° C. to about 80° C., from about 40° C. to about 150° C., from about 40° C. to about 120° C., from about 40° C. to about 100° C., from about 40° C. to about 80° C., from about 50° C. to about 150° C., from about 50° C. to about 120° C., from about 50° C. to about 100° C., from about 50° C. to about 80° C., from about 50° C. to about 70° C., from about 55° C. to about 65° C., or about 60° C.

The asphaltene precipitate-containing aqueous mixture in the tailing solvent recovery unit has a reduced yield stress as compared to an otherwise identical asphaltene precipitate-containing aqueous mixture without the water-soluble polymer when measured at a pressure from about 15 psi to about 150 psi, from about 15 psi to about 130 psi, from about 15 psi to about 110 psi, from about 15 psi to about 90 psi, from about 15 psi to about 80 psi, from about 30 psi to about 150 psi, from about 30 psi to about 130 psi, from about 30 psi to about 110 psi, from about 30 psi to about 90 psi, from about 30 psi to about 85 psi, from about 50 psi to about 150 psi, from about 50 psi to about 130 psi, from about 50 psi to about 110 psi, from about 50 psi to about 90 psi, from about 50 psi to about 85 psi, from about 70 psi to about 150 psi, from about 70 psi to about 130 psi, from about 70 psi to about 110 psi, from about 70 psi to about 90 psi, from about 70 psi to about 85 psi, from about 75 psi to about 85 psi, or about 80 psi.

When the yield stress is measured at a temperature from about 55° C. to about 65° C., a pressure from about 75 psi to about 85 psi, in a vane geometry rheometer at a rate of about 550 rpm to about 650 rpm, the viscosity is reduced by about 80%, about 75%, about 70%, about 65%, about 60%, about 55%, about 50%, about 45%, about 40%, about 35%, about 30%, about 25%, or about 20%.

The water-soluble polymer disperses the asphaltene/solid aggregates into the aqueous mixture.

The effective amount of the water-soluble polymer can be from about 20 ppm to about 500 ppm, from about 20 ppm to about 400 ppm, from about 20 ppm to about 300 ppm, from about 20 ppm to about 200 ppm, from about 20 ppm to about 100 ppm, from about 50 ppm to about 500 ppm, from about 50 ppm to about 400 ppm, from about 50 ppm to about 300 ppm, from about 50 ppm to about 200 ppm, from about 50 ppm to about 100 ppm, from about 80 ppm to about 500 ppm, from about 80 ppm to about 400 ppm, from about 80 ppm to about 300 ppm, from about 80 ppm to about 200 ppm, from about 80 ppm to about 150 ppm, from about 80 ppm to about 120 ppm, based on the total weight of the aqueous mixture comprising asphaltene/solid aggregates.

The water-soluble polymer can comprise a polyanion, a polycation, a polar water-soluble polymer.

The water-soluble polymer can comprise a polyanion.

The polyanion can comprise a polyacrylic acid, poly (methyl methacrylate), a polystyrene carboxylic acid, a poly(maleic acid), a polystyrene sulfonic acid, a polyvinyl sulfonic acid, a poly(2-acrylamido-2-methylpropane sulfonic acid), a poly(3-acrylamido-3-methylbutanoic acid), or a combination thereof.

The water-soluble polymer can comprise a sulfonated water-soluble polymer.

The water-soluble polymer can comprise a polystyrene sulfonic acid, a polyvinyl sulfonic acid, a poly(2-acrylamido-2-methylpropane sulfonic acid), a poly(3-acrylamido-3-methylbutanoic acid), or a combination thereof.

The water-soluble polymer can comprise a polystyrene sulfonic acid.

The water-soluble polymer can comprise a poly(styrene sulfonic acid-co-maleic acid).

The water-soluble polymer can comprise a polycation.

The water-soluble polymer can comprise poly(melamine formaldehyde), poly(diallyldimethylammonium chloride), poly(diallyldiethylammonium chloride), poly(diethylaminoethyl methacrylate), poly(dimethylaminoethyl methacrylate), poly(methacryloyloxyethyltrimethyl ammonium sulfate), poly(methacryloyloxyethyltrimethyl ammonium chloride), poly(3-(methyacrylamido)propyltrimethyl ammonium chloride), or a combination thereof.

The water-soluble polymer can comprise poly(melamine formaldehyde).

The water-soluble polymer can comprise a polar water-soluble polymer.

The polar water-soluble polymer comprises polyacrylamide, a poly(vinyl alcohol), a poly(vinvylpyrrolidone), or a poly(hydroxymethyl acrylate), or a combination thereof.

Another aspect of method for determining viscosity, yield stress, or viscosity and yield stress of an asphaltene precipitate-containing aqueous mixture comprising charging a bitumen froth into a high pressure reactor fitted with a mixer and a temperature controller; charging a paraffinic solvent into a sampling cylinder in fluid contact with the high pressure reactor; heating the high pressure reactor to a temperature of from about 30° C. to about 95° C.; pressurizing the high pressure reactor by adding gas from a gas source in fluid contact with the high pressure reactor; contacting the paraffinic solvent with the bitumen froth to form a reaction mixture; mixing the reaction mixture; stopping the mixing and allowing the solids, water, and asphaltene precipitates to separate from the bitumen forming a bitumen layer and an aqueous layer; removing at least a portion of the bitumen layer from the high pressure reactor; contacting an effective amount of a water-soluble polymer for reducing viscosity, yield stress, or viscosity and yield stress with the aqueous layer; contacting additional paraffinic solvent with the remaining bitumen layer and aqueous layer to form a second reaction mixture; reheating the high pressure reactor to a temperature of from about 30° C. to about 95° C.; repressurizing the high pressure reactor by adding gas from a gas source in fluid contact with the high pressure reactor; mixing the second reaction mixture; stopping the mixing and allowing the water and asphaltene precipitates to separate from the bitumen forming a second bitumen layer and a second aqueous layer; removing at least a portion of the second bitumen layer from the high pressure reactor; and measuring viscosity, yield stress, or viscosity and yield stress of the second aqueous layer.

The paraffinic solvent is a $C_5$ to $C_7$ paraffinic hydrocarbon solvent or a combination thereof.

The temperature within the high pressure reactor ranges from about 30° C. to about 95° C., from about 30° C. to about 85° C., from about 30° C. to about 75° C., from about 40° C. to about 95° C., from about 40° C. to about 85° C., from about 40° C. to about 75° C., from about 50° C. to about 95° C., from about 50° C. to about 85° C., or from about 50° C. to about 75° C.

The absolute pressure within the high pressure reactor is from about 50 psi to about 200 psi, from about 50 psi to about 180 psi, from about 50 psi to about 160 psi, from about 50 psi to about 150 psi, from about 70 psi to about 200 psi, from about 70 psi to about 180 psi, from about 70 psi to about 150 psi, from about 100 psi to about 200 psi, from about 100 psi to about 180 psi, or from about 100 psi to about 150 psi.

The inert gas is nitrogen, argon, helium, or a combination thereof. Preferably, the inert gas is nitrogen.

Having described the invention in detail, it will be apparent that modifications and variations are possible without departing from the scope of the invention defined in the appended claims.

EXAMPLES

The following non-limiting examples are provided to further illustrate the present invention.

Example 1

High Temperature Paraffinic Froth Treatment (HTPFT)

Figure 2:
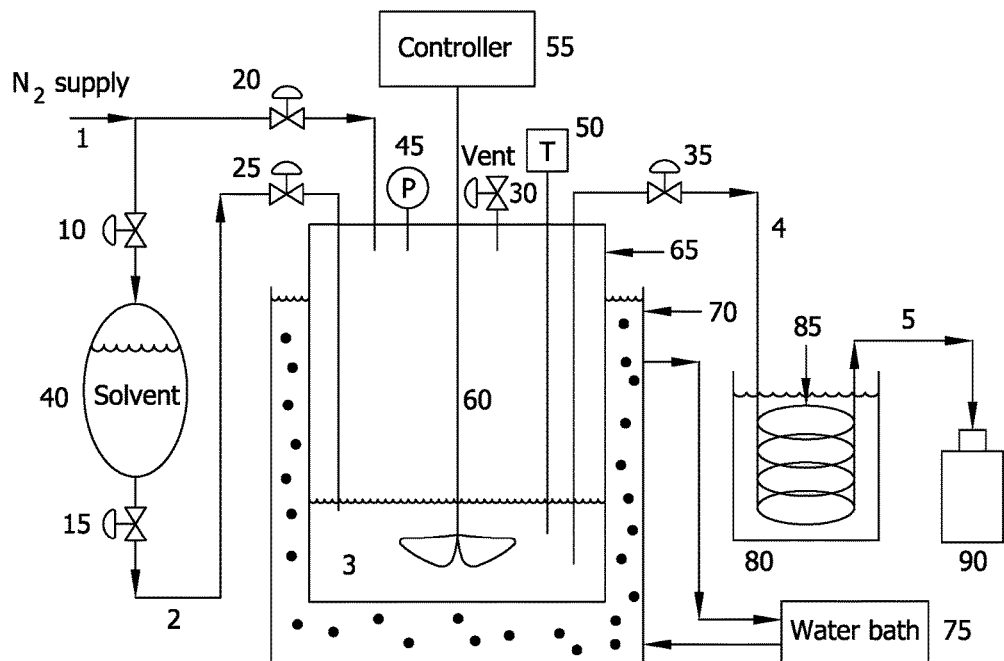
FIG. 2 is a diagram of a laboratory bench unit used to simulate the paraffinic froth treatment process.

A simple laboratory bench unit was designed and built to evaluate treatment methods and new chemistries. This laboratory bench unit is represented by FIG. 2, which comprises a bench top reactor 65, a magnetic drive or mixer 60 with a power controller 55, a water bath 75 connected to a water jacket 70, a sampling cylinder 40, an ice bath 80, a cooling coil 85, an overflow sample collector 90, connecting lines and valves and an inert gas cylinder with a pressure regulator.

The testing apparatus is used to evaluate various methods and new chemistries to obtain data with respect to performance and various method parameters (i.e., temperature, concentration, and time).

Froth samples were collected, divided into 120 g samples, and analyzed using a Dean-Stark apparatus for various components (e.g., bitumen, water, and solids content).

The amount of paraffinic solvent needed was based on the type of solvent and the solvent to bitumen ratio (S/B).

The test method consisted of placing a reactor vessel 65 into a water jacket 70 that was preheated to 90° C. A 120 g sample of froth was placed into a glass jar and heated to 70° C. using a separate water bath. A paraffinic solvent was then added into a sampling cylinder 40 through the funnel, followed by closing both valves and increasing the temperature to 70° C. Once the glass jar containing the froth sample reached 70° C., it was then poured into the reactor vessel 65.

At this point, known as chemical injection point one, a desired amount of water-soluble polymer was added into the reactor vessel 65.

The reactor vessel 65 was then placed on its holder, engaged, and secured to the head unit. The water jacket 70 was then placed underneath the reactor vessel 65 in order to maintain the desired operating temperature. An inert gas was then added through line 1 and valve 20 to the reaction vessel 65 in order to increase the pressure to 80 psi. Following a leak check, the inert gas was vented from the reactor 65 through the vent valve 30 and the vent valve 30 was returned to the closed position. The bottom of the warmed sampling cylinder 40 was then connected to the sample inlet line 2 of the reactor vessel 65. The gas supply was then connected to the top side of the sampling cylinder 40 through valve 10. When the gas valve 10 was opened, the sampling cylinder 40 became pressurized which forced the hot paraffinic solvent into the reactor vessel 65. After the pressure inside the reactor vessel 65 reached 110 psi, the inlet valve 10 on the sampling cylinder was closed. After the reactor vessel 65 temperature reached 75° C., the motor was set to 40% power and turned on. The mixer speed was then set at 600 rpm. After five minutes of mixing, the motor was turned off. Once the solids/water/asphaltene aggregates settled, approximately two minutes, the sample outlet valve 35 was opened to allow the flow of the first stage overflow. The overflow was then collected after it passed through a cooling coil 85 immersed in an ice bath. After the pressure within the reactor vessel had dropped to 40 psi, the sample outlet valve 35 was closed.

At this point, known as chemical injection point two, a desired amount of a water-soluble polymer could be added to the inlet line 2 without opening the reaction vessel 65.

Hot paraffinic solvent was then added to the reactor vessel 65 by pairing it with a pre-heated pressure cylinder to the inlet line 2. An inert gas was used to pressurize the cylinder. The reactor vessel 65 was heated to 70° C. After the reactor vessel 65 reached the desired temperature, the motor was turned on and allowed to mix the contents for five minutes. Once the solids/water/asphaltene aggregates settled, approximately two minutes, the sample outlet valve 35 was opened to allow the flow of the second stage overflow. The overflow was then collected after it passed through a cooling coil 85 immersed in an ice bath. After the pressure within the reactor vessel had dropped to 40 psi, the sample outlet valve 35 was closed.

At this point, also known as chemical injection point three, without opening the reaction vessel 65, a desired amount of a water-soluble polymer could be added to the inlet tubing 2 through valve 15. Nitrogen supply line 1 was used to pressurize the water-soluble polymer into the vessel 65.

The impeller was run at 600 rpm for three minutes followed by depressurizing the system. After depressurizing, the vessel was opened and the second stage underflow sample was collected. The remaining tailings were removed with toluene and transferred to a HDPE bottle.

The first and second stage overflow samples were subjected to Karl Fisher water content, solids/ash, and asphaltene suspension determination.

The temperature of the reactor vessel and sampling cylinder was measured using a Type J thermocouple.

Example 2

Evaluation of Compositions Using the Bench-scale HTPFT Setup

The bench-scale HTPFT setup was used to evaluate compositions for their efficacy of increasing the fluidity of underflow stream and solvent recovery. The composition tested comprised 89.6595 wt. % water, 0.3959 wt. % hydroxymethyl urea, 0.3959 wt. % N,N'-bis(hydroxymethyl) urea, 0.9895 wt. % hydrochloric acid, 7.9162 wt. % formaldehyde-melamine copolymer hydrochloride, 0.09 wt. % formaldehyde, and 0.553 wt % melamine formaldehyde resin (identified as composition A hereinafter and commercially available from Nalco as Product No. PK-9512).

The bench-scale HTPFT setup was used to evaluate composition A using the method described in Example 1. The key parameters used during the testing procedure are shown in Table 1. The amount of composition A used was 100 ppm of water-soluble polymer based on the total aqueous mixture treated.

TABLE 1

Bench-scale HTPFT test parameters for composition A.

| | |
|---|---|
| Temperature | 60° C. |
| Pressure | 80 psi |
| 1$^{st}$ stage D/B (wt./wt., diluent to bitumen ratio) | 1.75 |
| 2$^{nd}$ stage D/B (wt./wt.) estimation | 20 |
| Mixing at 1$^{st}$ and 2$^{nd}$ stage | 600 rpm for 5 min. |

A summary of the test results are shown in Table 2.

TABLE 2

Bench-scale HTPFT test results using compositions A.

| Simulation | | Blank | 100 ppm of A added to 1$^{st}$ stage underflow | 100 ppm of A added to 2$^{nd}$ stage underflow | 100 ppm of A added to froth |
|---|---|---|---|---|---|
| Test number | | 1 | 2 | 3 | 4 |
| Water % in first stage overflow | | 0.20% | 0.35% | 0.25% | 0.06% |
| Asphaltene suspension % in first stage overflow | | 1.8% | 1.6% | 1.6% | 1.8% |
| Solids content % in first stage overflow (volume reading) | | ~250 ppm | ~250 ppm | ~250 ppm | ~250 ppm |
| Maltene/asphaltene % in second underflow | | 25.6% | 22.7% | 24.7% | 50.0% |
| Physical appearance of second underflow | Color | Shining black | Black | Matt black | Black |
| | Size | Relatively big | Medium | Medium | Small |
| | Shape | Irregular | Granular | Granular | Granular |
| | Stickiness | Medium | Low | Low | Medium |

Example 3

Evaluation of Compositions by Rheology Analysis of Underflow Samples Using the HTPFT Apparatus The bench scale HTPFT setup was used to evaluate various compositions for their efficacy of enhancing the rheology of underflow streams using the method described in Example 1. The compositions tested comprised composition A, 82 wt. % water and 18 wt. % polystyrene sulfonic acid (identified as composition B hereinafter), 75 wt. % water and 25 wt. % poly(styrene sulfonic acid-co-maleic acid) (identified as composition C hereinafter).

The key parameters used during the testing procedure are shown in Table 1. A summary of the rheology test results are shown in Table 3.

TABLE 3

Bench scale HTPFT rheology test results

| Sample | Yield stress (Pa) | Viscosity (cP) |
|---|---|---|
| Blank | 187 | 341 |
| A | 48 | 125 |
| B | 39 | 92 |
| C | 35 | 83 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying drawing shall be interpreted as illustrative and not in a limiting sense.

What is claimed is:

1. A method for decreasing viscosity, yield stress, or viscosity and yield stress of an asphaltene precipitate-containing aqueous mixture comprising mixing an asphaltene-containing hydrocarbon with a paraffinic solvent to form the asphaltene precipitate-containing aqueous mixture and contacting an effective amount of a water-soluble polymer with the asphaltene precipitate-containing aqueous mixture whereby the viscosity, yield stress, or viscosity and yield stress of the asphaltene precipitate-containing aqueous mixture is reduced as compared to an otherwise identical asphaltene precipitate-containing aqueous mixture without the water-soluble polymer when measured at a temperature from about 20° C. to about 150° C., wherein the water-soluble polymer disperses the asphaltene precipitates into the aqueous mixture and the effective amount of the water-soluble polymer is from about 20 ppm to about 500 ppm based on the total weight of the asphaltene precipitate-containing aqueous mixture.

2. The method of claim 1 wherein the asphaltene precipitate-containing aqueous mixture is from the underflow of a froth settling unit in a paraffinic solvent froth treatment.

3. The method of claim 2 wherein the underflow is from a second froth settling unit in the paraffinic solvent froth treatment.

4. The method of claim 3 wherein the underflow from the second froth settling unit is transferred to a tailings solvent recovery unit.

5. The method of claim 4 wherein the asphaltene precipitate-containing aqueous mixture in the tailings solvent recovery unit has a reduced viscosity as compared to an otherwise identical asphaltene precipitate-containing aqueous mixture without the water-soluble polymer when measured at a temperature from about 20° C. to about 150° C.

6. The method of claim 4 wherein the asphaltene precipitate-containing aqueous mixture in the tailings solvent recovery unit has a reduced yield stress as compared to an otherwise identical asphaltene precipitate-containing aqueous mixture without the water-soluble polymer when measured at a temperature from about 20° C. to about 150° C.

7. The method of claim 1 wherein the water-soluble polymer comprises a polyanion and the polyanion comprises a polyacrylic acid, poly(methyl methacrylate), a polystyrene carboxylic acid, a poly(maleic acid), a polystyrene sulfonic acid, a polyvinyl sulfonic acid, a poly(2-acrylamido-2-methylpropane sulfonic acid), a poly(3-acrylamido-3-methylbutanoic acid), or a combination thereof.

8. The method of claim 1 wherein the water-soluble polymer comprises a sulfonated water-soluble polymer.

9. The method of claim 1 wherein the water-soluble polymer comprises a polystyrene sulfonic acid, a polyvinyl sulfonic acid, a poly(2-acrylamido-2-methylpropane sulfonic acid), a poly(3-acrylamido-3-methylbutanoic acid), or a combination thereof.

10. The method of claim 9 wherein the water-soluble polymer comprises a polystyrene sulfonic acid.

11. The method of claim 10 where the water-soluble polymer comprises a poly(styrene sulfonic acid-co-maleic acid).

12. The method of claim 1 wherein the water-soluble polymer comprises a polar water-soluble polymer and the polar water-soluble polymer comprises a polyacrylamide, a poly(vinyl alcohol), a poly(vinvylpyrrolidone), or a poly(hydroxymethyl acrylate), or a combination thereof.

13. The method of claim 1 wherein the water-soluble polymer comprises a polycation and the water-soluble polymer comprises poly(melamine formaldehyde), poly(diallyldimethylammonium chloride), poly(diallyldiethylammonium chloride), poly(diethylaminoethyl methacrylate), poly(dimethylaminoethyl methacrylate), poly(methacryloyloxyethyltrimethyl ammonium sulfate), poly(methacryloyloxyethyltrimethyl ammonium chloride), poly(3-(methyacrylamido)propyltrimethyl ammonium chloride), or a combination thereof.

14. The method of claim 13 wherein the water-soluble polymer comprises poly(melamine formaldehyde).

15. A method for determining viscosity, yield stress, or viscosity and yield stress of an asphaltene precipitate-containing aqueous mixture comprising
charging a bitumen froth into a high pressure reactor fitted with a mixer and a temperature controller;
charging a paraffinic solvent into a sampling cylinder in fluid contact with the high pressure reactor;
heating the high pressure reactor to a temperature of from about 30° C. to about 95° C.;
pressurizing the high pressure reactor by adding gas from a gas source in fluid contact with the high pressure reactor;
contacting the paraffinic solvent with the bitumen froth to form a reaction mixture;
mixing the reaction mixture;
stopping the mixing and allowing the solids, water, and asphaltene precipitates to separate from the bitumen forming a bitumen layer and an aqueous layer;
removing at least a portion of the bitumen layer from the high pressure reactor;
contacting an effective amount of a water-soluble polymer for reducing viscosity, yield stress, or viscosity and yield stress with the aqueous layer;
contacting additional paraffinic solvent with the remaining bitumen layer and aqueous layer to form a second reaction mixture;
reheating the high pressure reactor to a temperature of from about 30° C. to about 95° C.;
repressurizing the high pressure reactor by adding gas from a gas source in fluid contact with the high pressure reactor;
mixing the second reaction mixture;
stopping the mixing and allowing the water and asphaltene precipitates to separate from the bitumen forming a second bitumen layer and a second aqueous layer;
removing at least a portion of the second bitumen layer from the high pressure reactor; and
measuring viscosity, yield stress, or viscosity and yield stress of the second aqueous layer.

16. The method of claim 15 wherein the paraffinic solvent comprises a $C_5$ to $C_7$ paraffinic hydrocarbon solvent or a combination thereof.

17. The method of claim 15 wherein the temperature within the high pressure reactor ranges from about 30 to about 95° C.

18. The method of claim 15 wherein the absolute pressure within the high pressure reactor is from about 80 to about 130 psi.

19. The method of claim 15 wherein the high pressure reactor is pressured with an inert gas.

* * * * *

UNITED STATES PATENT AND TRADEMARK OFFICE
CERTIFICATE OF CORRECTION

PATENT NO. : 10,400,180 B2
APPLICATION NO. : 15/282285
DATED : September 3, 2019
INVENTOR(S) : Ali Faghihnejad Page 1 of 1

It is certified that error appears in the above-identified patent and that said Letters Patent is hereby corrected as shown below:

In the Claims

On Column 9, Claim 12, Line 63:
"poly(vinvylpyrrolidone)" should read "poly(vinylpyrrolidone)"

On Column 10, Claim 13, Lines 8-9:
"poly(3-(methyacrylamido)propyltrimethyl ammonium chloride" should read "poly(3-(methacrylamido) propyltrimethyl ammonium chloride"

On Column 10, Claim 17, Line 57:
"30" should read "30° C."

Signed and Sealed this
Fifteenth Day of December, 2020

Andrei Iancu
*Director of the United States Patent and Trademark Office*